United States Patent [19]

Sutter, Jr. et al.

[11] Patent Number: 4,878,894
[45] Date of Patent: Nov. 7, 1989

[54] GAS/SALINE VALVE WITH SUCTION CONTROL

[76] Inventors: Leroy V. Sutter, Jr., 44 Rocky Knoll, Irvine, Calif., 92715; Harold A. Cameron, 2382 Morse Ave., Irvine, Calif., 92714

[21] Appl. No.: 19,434

[22] Filed: Feb. 26, 1987

[51] Int. Cl.$^4$ .................... A61B 17/36; A61M 1/00
[52] U.S. Cl. ........................ 604/24; 604/32; 604/34; 604/119; 604/248; 604/250
[58] Field of Search ............... 604/23.24, 27, 28, 30, 604/32–35, 118–120, 246, 248–250; 128/747; 251/4, 6–10

[56] References Cited

U.S. PATENT DOCUMENTS

| | | | |
|---|---|---|---|
| 3,208,145 | 9/1965 | Turner | 604/119 |
| 3,215,394 | 11/1965 | Sherman | 251/4 |
| 3,316,935 | 5/1967 | Kaiser et al. | 251/4 |
| 3,515,170 | 6/1970 | Mullaly | 251/7 |
| 3,769,962 | 11/1973 | McVey | 604/24 |
| 4,312,493 | 1/1982 | Stauffer | 604/34 |
| 4,331,130 | 5/1982 | Lewicky | 604/23 |
| 4,402,310 | 9/1983 | Kimura | 604/30 |
| 4,668,215 | 5/1987 | Allgood | 604/30 |
| 4,715,372 | 12/1987 | Philippbar | 128/303.1 |

*Primary Examiner*—C. Fred Rosenbaum
*Attorney, Agent, or Firm*—W. Edward Johansen

[57] ABSTRACT

The present invention is a gas/saline valve for use in an gas/saline insufflation system which includes a gas insufflator and a saline source. The gas insufflator is fluidly coupled to a gas inlet of an arthroscopic attachment by a first tubing. The saline source is fluidly coupled to a saline inlet of an arthroscope by a second tubing. The gas/saline valve includes a housing with an open end and a gas/saline control knob. The housing has a first bore and a second bore. The housing also has a first slotted chamber and a second slotted chamber both of which are contiguous to the first and second bores, respectively, and within which the first and second tubings, respectively, are disposed. The gas/saline control knob has a solid cylinder which has a first semi-cylindrical notch and a second semi-cylindrical notch so that when the solid cylinder is disposed inside the housing, the first and second semi-cylindrical notches are aligned with the first and second slotted chambers, respectively. When an unnotched portion of the solid cylinder is contiguous to the first or second tubing, it compresses the tubing into the first or second slotted chamber thereby closing off the flow of gas or saline, respectively, therein and when the first or second semi-cylindrical notch becomes contiguous to the first or second tubing, respectively, the tubing is no longer compressed thereby maintaining or turning on the flow of gas or saline, respectively, therethrough.

2 Claims, 4 Drawing Sheets

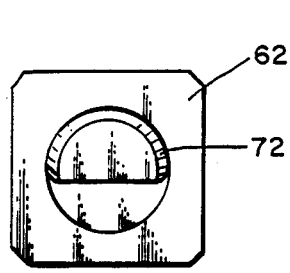
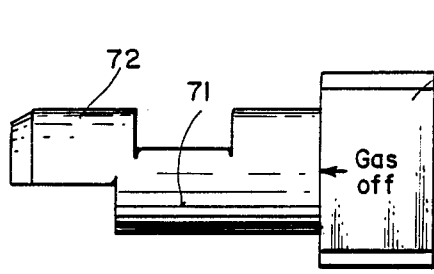
Fig. 8.    Fig. 7.
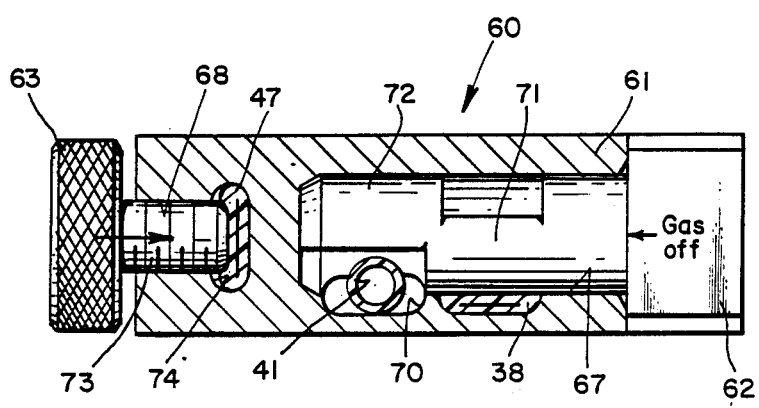
Fig. 9.
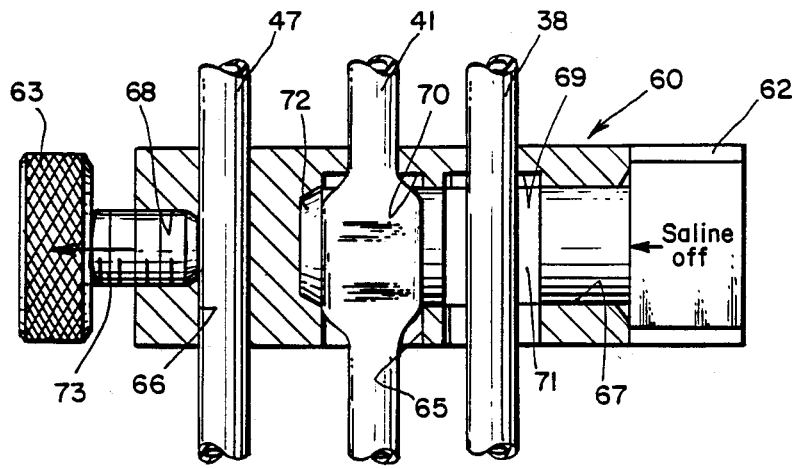
Fig. 10.

GAS/SALINE VALVE WITH SUCTION CONTROL

BACKGROUND OF THE INVENTION

1. Field of the Invention

The present invention relates to a gas/saline insufflation system for distending a knee joint, a shoulder joint, an elbow joint, an ankle joint or a wrist and more particularly to a gas/saline valve with suction control which a surgeon uses to efficiently change between a saline environment and a gas environment during diagnostic arthroscopy and laser arthroscopic surgery.

2. Description of the Prior Art

In their article, entitled "Laser Energy in Arthroscopic Meniscectomy," published in *Orthopedics*, Volume 6, Number 9, pages 1165-1169, September, 1983, Terry L. Whipple, Richard B. Caspari and John F. Meyers discussed the rationale and technique for performing arthroscopic meniscectomy with a carbon dioxide laser system. They distended the knee joint with either nitrogen or carbon dioxide through the sleeve of the arthroscope via a gas infusion pump, which maintained the intra-articular pressure in the range of 80 to 100 mm Hg. Before they introduced the laser cannula through a separate portal, they switched the gas infusion to the laser cannula in order to prevent liquid or particulates from entering the laser cannula.

U.S. Pat. No. 4,369,768, entitled Arthroscope, issued to Marko Vukovic on Jan. 25, 1983, teaches an arthroscope. U.S. Pat. No. 3,769,962, entitled Barium Enema Administration Method and Apparatus, issued to Raymond McVey on Nov. 6, 1973, teaches a barium enema administration apparatus which includes a first conduit, a second conduit and a third conduit all are connected together at three-way union. The first conduit is connected to a gravity fed barium supply source. The second conduit is connected with a source of air under pressure. The third conduit is an evacuation line which is connected to a source of suction. Each conduit is controlled by an individual valve. The valves are opened and closed in a prescribed sequence as directed by a radiologist.

On July 29, 1986 Chadwick F. Smith and Leroy V. Sutter, Jr. filed an application, entitled Arthroscopic Attachment for Use with a Laser System, having Ser. No. 891,224, described an arthroscopic attachment. A laser system is optically and mechanically coupled to the arthroscopic attachment so that the arthroscopic attachment may be used surgically under arthroscopic control. The arthroscopic attachment includes a gas inlet for letting a gas into the arthroscopic attachment and a lens focusing system for focusing the beam of light energy into a guide member which also functions as a gas nozzle.

In their article, entitled "The Use of Laser Beams for Operations in Haemophilia," published in *The Scandinavian Journal of Haemotology* in 1984, Supplementum 40, Volume 33, pages 281-289, 1984 F. Hefti, E. Morscher and F. Koller used a Sharplan 791 CO2 Surgical Laser to perform five synovectomies of the knee joint, four synovectomies of the elbow joint and one splitting of the retinaculum of the knee joint.

U.S. Pat. No. 3,865,113, entitled Laser Device Particularly Useful as Surgical Scalpel, issued to Uzi Sharon and Isaac Kaplan on Feb. 11, 1975, teaches a laser beam manipulator including a tube which is optically coupled through an articulated arm to a carbon dioxide laser system and a beam targeting member which is carried by the tube.

U.S. Pat. No. 3,710,798, entitled Laser System for Microsurgery, issued to Herbert C. Bredemeier on Jan. 16, 1973, teaches a laser system for microsurgery which includes a mirror for changing the direction of a beam of light energy from a carbon dioxide laser system and directing the beam to the treatment site.

U.S. Pat. No. 3,982,541, entitled Eye Surgical Instrument, issued to Francis A. L'Esperance on Sept. 28, 1976, teaches a method of surgically removing body tissue which includes the steps of contacting the body tissue with a probe open at a free end, passing a carbon dioxide laser beam through a central passage in the probe and the open end to the tissue at a power level sufficent to affect vaporization of tissue, vaporizing only the surface portion of the tissue exposed to the carbon dioxide laser beam in a manner so that the vaporizing step is surface phenomena at a depth not more than about 0.33 millimeters, introducing a gas stream into the probe downstream from the lenses associated with the carbon dioxide laser beam, passing the gas stream through the probe in a direction towards its free end and out thereof, and removing smoke and any vaporized portion of the tissue through the probe by way of the gas stream.

U.S. Pat. No. 3,982,533, entitled Insufflation Apparatus, issued to F. M. Wiest on Sept. 28, 1976, teaches an apparatus for introducing limited quantities of carbon dioxide into the human body for operational purposes, particularly laparoscopy. The insufflation apparatus includes a control device for delivering the carbon dioxide, a connecting nipple on the control device for connecting a first flexible tubing to a first operative cannula of a dual Veress needle introducable into the body and a pressure gauge for indicating the pressure present in the body cavity. The insufflation apparatus also includes a second connection nipple which is disposed on the control device and which is connected by a nipple to a pressure gauge. The second connection nipple is connected by a second flexible tubing to a second coaxial cannula of the dual Veress needle so that the pressure gauge is directly connected with the body cavity rather through the first cannula of the dual Veress needle.

U.S. Pat. No. 4,048,992, entitled Insufflator, issued to Hans-Joachin Lindemann and F. M. Wiest on Sept. 20, 1977, teaches an apparatus for introducing limited quantities of carbon dioxide into the human body for operational purposes, particularly laparoscopy or hysteroscopy. The insufflation apparatus includes two pressure reducers, in series, followed by a gas flow monitoring device through which carbon dioxide is directed from a gas supply to a human body. The two pressure reducers are constantly adjusted to fixed gas supply pressures. The gas flow monitoring device includes a cylindrical expansion container which has a central inlet port and a large diameter, and in whose peripheral zone the gas flow velocity approaches a zero rate. First and second sensing elements for the measured variable are provided in the expansion container. The first sensing element is located immediately in the area of the inlet port and the second sensing element is located close to the cylindrical side wall at the maximum possible radial spacing from the first sensing element. The two sensing elements are included in a measuring bridge and a measuring amplifier is connected to the bridge output. An indicator of the rate of flow is connected to the amplifier output. The second pressure reducer may be adjusted to a supply pressure in the range of 15 to 200 mm Hg.

U.S. Pat. No. 3,709,214, entitled Gas Obturating Method, issued to Jack R. Robertson on Jan. 9, 1973, teaches a method of diagnosis and/or therapy of an internal part of the body which is accessible from an adjacent body opening. The method includes the step of introducing a gas under pressure into the adjacent body opening.

U.S. Pat. No. 4,550,240, entitled Laser Irradiating Apparatus, issued to Masahiro Toida and Norihiro Suenaga and Nobuyuki Suenaga on Oct. 29, 1985, teaches a laser irradiating apparatus which includes first and second light guides for two laser beams at a first wavelength and a second wavelength, respectively, and first and second supply for a first assist gas and a second assist gas, respectively.

U.S. Pat. No. 4,207,887, entitled Gas Insufflation Apparatus, issued to Siegfried Hiltebrandt and Helmut Wurster on July 17, 1980, teaches a gas insufflation apparatus which introduces limited quantities of carbon dioxide into a body cavity for operational purposes, particularly laparoscopy or hysteroscopy. The gas insufflation apparatus includes a compressed gas cylinder containing carbon dioxide, the pressure of which is controlled and monitored by a first pressure gauge and a first pressure regulator in series. From the first pressure regulator the gas flows at reduced pressure via a shut-off valve to an intermediate container the pressure and quantity of gas in which can be read off a second pressure gauge. The container also has a safety valve. The reduced-pressure insufflation gas from the container flows through a second pressure regulator which is advantageously continuously adjustable and by means of which the desired gas pressure in a body cavity required by a particular patient can be preselected. The regulated pressure can be monitored by a third pressure gauge. To inject a volume of gas into the body cavity, a valve downstream of the second pressure regulator is opened manually so that the gas will then flow to the body cavity via a rate of flow controller, an insufflation duct and a tube constituted by the cannula. The preselected pressure is maintained by the second pressure regulator.

U.S. Pat. No. 3,885,590, entitled Gas Transmission and Monitoring Device, entitled to John L. Ford on May 27, 1975, teaches a compact self-contained flow and pressure regulator device which transmits and monitors gas from a source of compressed gas to a body cavity during surgery. The device includes a selectively adjustable pressure regulator which controls the gas received from the compressed gas source, a limiting orifice to attenuate the flow rate and an off-on valve. The device also includes an adjustable pressure valve which controls the discharge gas pressure, a gauge which indicates the discharge gas pressure, and a safety relief valve.

On Dec. 15, 1986 Leroy V. Sutter, Jr. and Chadwick F. Smith filed an application, Ser. No. 941,165, entitled Self-Cleaning Suction Probe for Arthroscopic Surgery, which teaches a self-cleaning suction probe. The surgeon doing arthroscopic surgery uses the self-cleaning suction probe in an irrigation system in order to provide egress for saline and body fluid from an irrigation site.

U.S. Pat. No. 4,487,600, entitled Adjustable Suction Device for Medical Use, issued to Alan W. Brownlie and Roger D. Spier on Dec. 11, 1984, teaches an adjustable, disposable suction device which is particularly adapted for medical use. A surgeon uses the adjustable suction device to remove either excess blood or body fluids from an open incision during surgery.

U.S. Pat. No. 4,604,089, entitled Pressure Regulated Irrigation System for Arthroscopy, issued to John A. Santangelo and Charles B. Worrick on Aug. 5, 1986, teaches a pressure regulated system irrigation system which includes a reservoir of irrigation fluid, such as saline, a pump and catheters which provide access to and egress from the irrigation site.

SUMMARY OF THE INVENTION

In view of the foregoing factors and conditions which are characteristic of the prior art it is the primary object of the present invention to provide a gas/saline insufflation system which distends a knee joint, a shoulder joint, an elbow joint, an ankle joint or a wrist.

It is another object of the present invention to provide a gas/saline valve with suction control which a surgeon uses to efficiently change between a saline environment and a gas environment during diagnostic arthroscopy and laser arthroscopic surgery.

In accordance with the preferred embodiment of the present invention a gas/saline valve for use in a gas/saline insufflation system is described. The gas/saline insufflation system includes a gas insufflator and a saline source. The gas insufflator is fluidly coupled to a gas inlet of an arthroscopic attachment by a first tubing. The saline source is fluidly coupled to a saline inlet of an arthroscope by a second tubing. The gas/saline valve includes a housing with an open end and a gas/saline control knob. The housing has a first bore and a second bore. The housing also has a first slotted chamber and a second slotted chamber both of which are contiguous to the first and second bores, respectively, and within which the first and second tubings, respectively, are disposed. The gas/saline control knob has a solid cylinder which has a first semi-cylindrical notch and a second semi-cylindrical notch so that when the solid cylinder is disposed inside the housing, the first and second semi-cylindrical notches are aligned with the first and second slotted chambers, respectively. When an unnotched portion of the solid cylinder is contiguous to the first or second tubing, it compresses the tubing into the first or second slotted chamber thereby closing off the flow of gas or saline, respectively, therein and when the first or second semi-cylindrical notch becomes contiguous to the first or second tubing, respectively, the tubing is no longer compressed thereby maintaining or turning on the flow of gas or saline, respectively, therethrough.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 7 is a side elevation of the gas/saline control knob of the gas/saline valve with suction control of FIG. 2.

FIG. 8 is a end view of the gas/saline control knob of the gas/saline valve with suction control of FIG. 2.

FIG. 9 is a side elevation in cross-section of the gas/saline valve with suction control of FIG. 2 in which the flow of saline is turned on, the flow of gas is closed off and the suction is closed off.

FIG. 10 is a top view in cross-section of the gas/saline valve with suction control of FIG. 2 in which the flow of saline is closed off, the flow of gas is turned on and the suction is turned on.

DESCRIPTION OF THE PREFERRED EMBODIMENT

Figure 1:
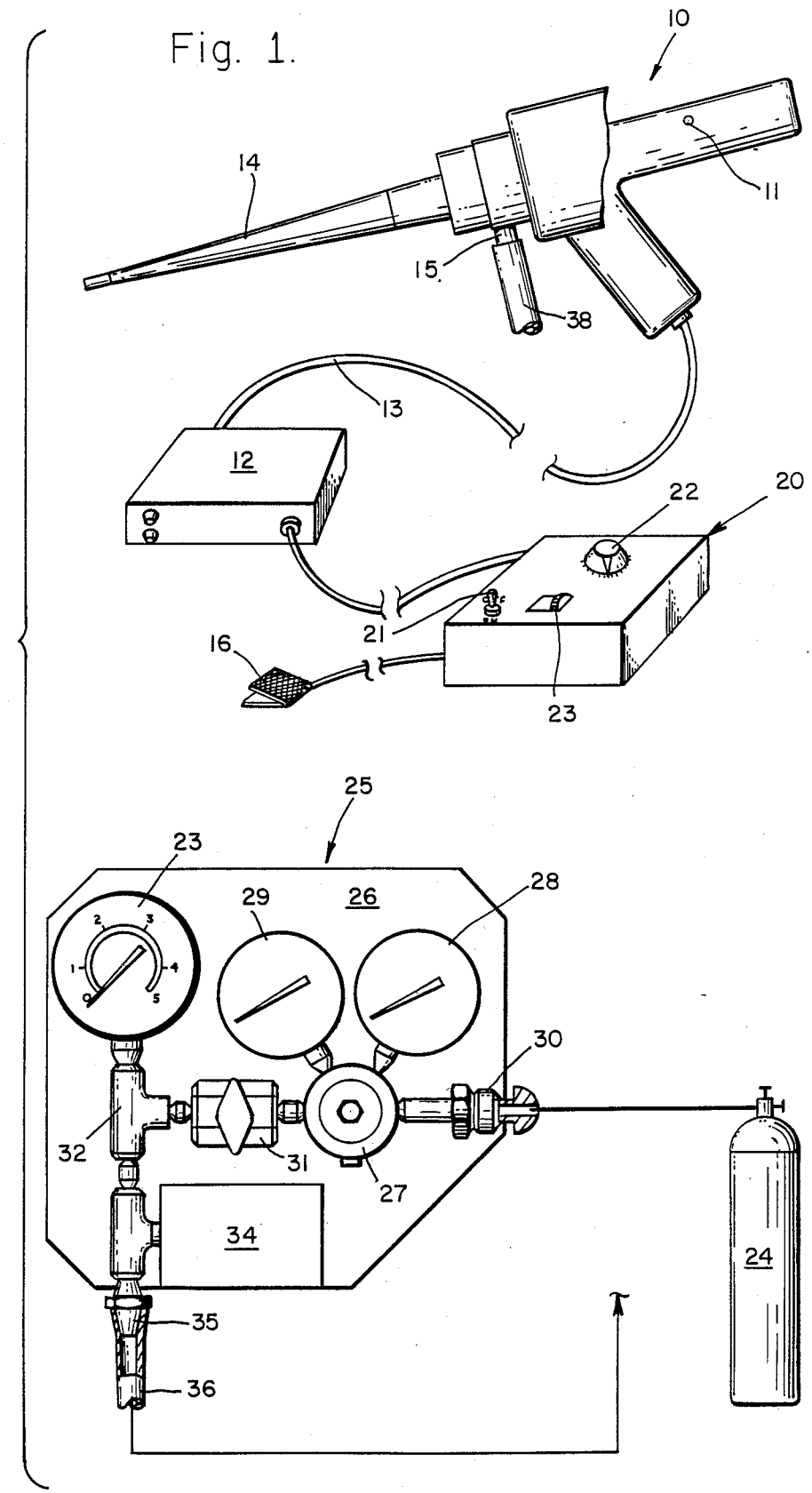
FIG. 1 is a perspective drawing of a hand held laser system and an arthroscopic attachment and a schematic drawing of a power supply, an electronic controller and a gas insufflator.

In order to best understand the present invention it is necessary to refer to the following description of its preferred embodiment in conjunction with the accompanying drawing. Referring to FIG. 1 a hand-held laser system 10 includes a laser output head 11, a power supply 12, a connector 13 which electrically couples the power supply 12 to the laser output head 11 and an arthroscopic attachment 14 which is mechanically and optically coupled to the laser output head 11. The arthroscopic attachment 14 has a gas inlet 15. A foot switch 16 is electrically coupled to the power supply 12 through an electronic controller 20 which may be used in combination with the hand-held laser system 10 to control the duration of each output beam of light energy from the hand-held laser system 10 within a range of 0.005 seconds to 0.100 seconds and to limit the maximum number of pulses to a number which a surgeon may select for use in surgical procedures. The electronic controller 20 has an on/off switch 21, a pulse width setting switch 22 and a selector switch 23 for selecting the number of pulses. An orthopedic surgeon uses the hand-held laser system 10 to perform surgery under arthroscopic control.

Still referring to FIG. 1 a cylinder 24 contains a gas, such as helium, nitrogen or carbon dioxide, at a high pressure. A gas insufflator 25 includes a plate 26 and a regulator 27 which has an inlet and an outlet and which is mounted on the plate 26. The regulator 27 has a cylinder pressure gauge 28 and regulator pressure gauge 29 fluidly coupled thereto. A gas coupling 30 which includes a filter fluidly couples the cylinder 24 to the inlet of the regulator 27. The gas insufflator 25 also includes a main valve 31 which has an inlet and an outlet and the inlet of which is fluidly coupled to the outlet of the regulator 27, a T-fitting 32 which has an inlet and two outlets and the inlet of which is fluidly coupled to the outlet of the main valve 31 and a patient pressure gauge 33 which is fluidly coupled to one of the outlets of the T-fitting 32. The gas insufflator 25 further includes a relief valve 34 and a gas port 35 both of which are fluidly coupled to the other outlets of the T-fitting 32.

Figure 2:
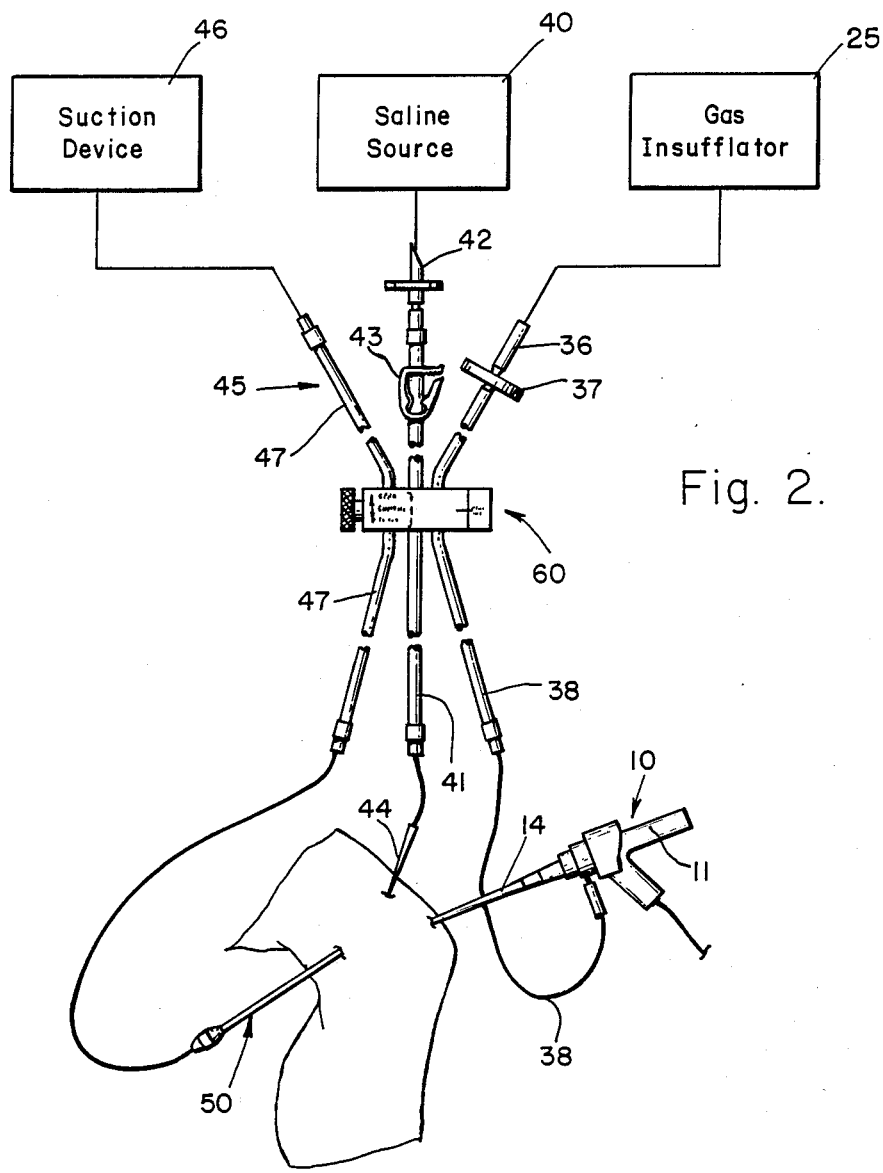
FIG. 2 is a schematic drawing of a gas/saline insufflation system which includes a gas/saline valve with suction control which has been constructed in accordance with the principles of the preferred embodiment of the present invention.

Referring to FIG. 2 in conjunction with FIG. 1 the gas insufflator 25 is used to distend the knee joint during arthroscopic surgery. The gas insufflator 25 includes a gas insufflator-output tubing 36 one end of which is fluidly coupled to the gas port 35, a filter 37 which is fluidly coupled to the other end of the gas insufflator-output tubing 36, a first tubing 38 one end of which is fluidly coupled to the filter 37. The other end of the first tubing 38 is fluidly coupled to the gas inlet 15 of the arthroscopic attachment 14.

Referring to FIG. 2 a saline insufflator 39 includes a saline source 40 and a second tubing 41 which one end of which has a hollow puncture-extrusion 45 for fluidly coupling the second tubing 41 to the saline source 40. A pinch clip 43 is mechanically coupled to the second tubing in order to pinch-off the flow of saline from the saline source 40. The other end of the second tubing 41 is fluidly coupled to a fluid inlet of an arthrscope 44. U.S. Pat. No. 4,369,768 teaches an arthroscope. The saline insufflator 39 is used to distend the knee joint during diagnostic arthroscopy.

Figure 3:
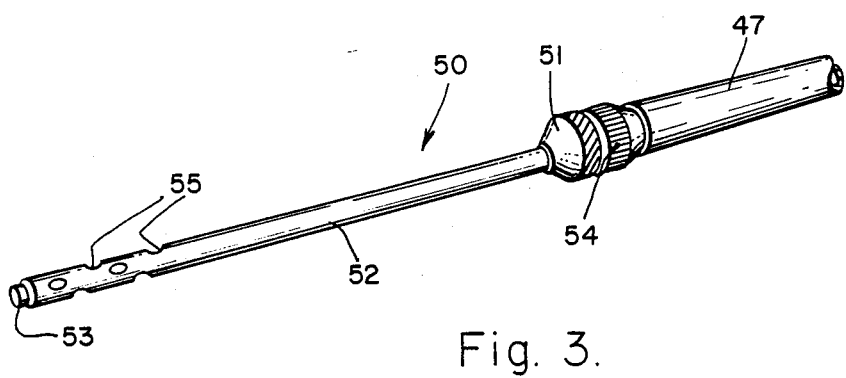
FIG. 3 is a perspective drawing of a self-cleaning suction probe which is used in combination with a suction device during arthroscopic surgery in an irrigation system.

Referring to FIG. 2 in conjunction with FIG. 3 an irrigation system 45 includes a suction device 46 and a third tubing 47 which has two ends and one end of which is fluidly coupled to the suction device 46. The other end is fluidly coupled to a self-cleaning suction probe 50 which includes a hollow handle 51, an outer tube 52, an inner tube 53 and a connector 54. The outer tube 52 is rigid and is connected at one end to the hollow handle 51. The outer tube 52 has a plurality of longitudinally spaced radial apertures 55 which are adjacent to its free end. The apertures 55 collect so much organic debris during arthroscopic surgery that the surgeon needs to clean them in order to maintain the outflow of saline and body fluid. The inner tube 53 is coaxially diposed within and slideably coupled to the outer tube 52. The connector 54 connects the third tubing 47 to the inner tube 53. The connector 54 is securely coupled to the inner tube 53 and rotatively coupled to the hollow handle 51. The inner tube 53 has a cutting blade which is fixedly coupled to the inner tube 53 at its distal end and which is contiguous to the aperatures 55. The surgeon by holding the hollow handle 51 and rotating the connector 54 rotates the cutting blade thereby cleaning the apertures without removing the self-cleaning suction probe 50 from the irrigation site and interrupting surgery. The surgeon can clean the selfcleaning suction probe 50 without inhibiting the outflow of saline and body fluid. A surgeon doing arthroscopic surgery uses the irrigation system 45 for providing egress from an irrigation site. A gas/saline valve with suction control 60 is mechanically coupled to the first, second and third tubings 38, 41, and 47 in order to both selectively either turn on or close off the gas and/or the saline and either turn on or close off suction in the irrigation system 45.

Figure 4:
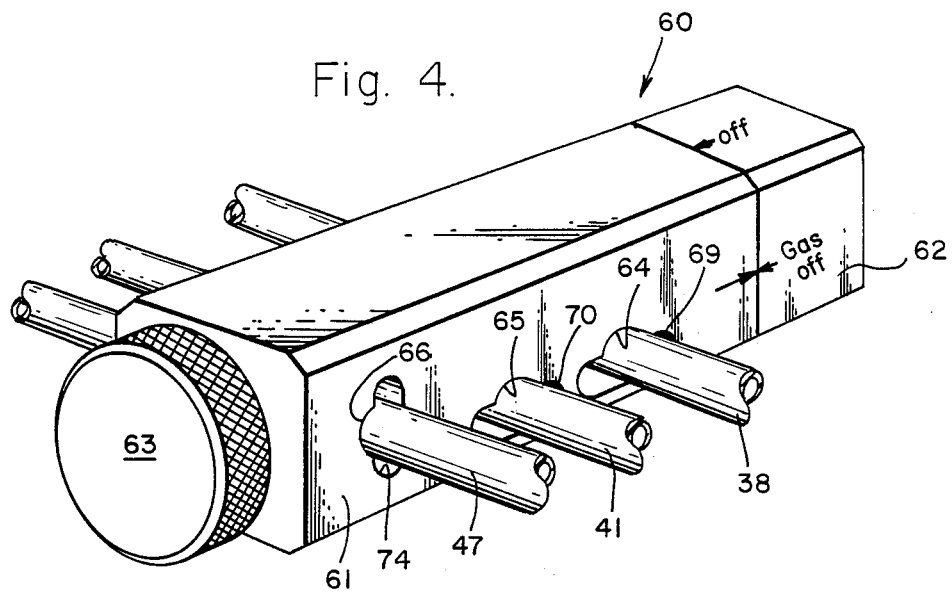
FIG. 4 is a perspective drawing of the gas/saline valve with suction control of FIG. 2 which includes a housing, a gas/saline control knob and a suction control knob.

Referring to FIG. 4 in conjunction with FIG. 2 the gas/saline valve 60 with suction control includes a housing 61, a gas/saline control knob 62 and a suction control knob 63. The housing 61 has a first bore 64, a second bore 65 and a third bore 66. The first, second and third tubings 38, 41, and 47 are disposed in the first, second and third bore 64, 65 and 66, respectively.

Figure 6:
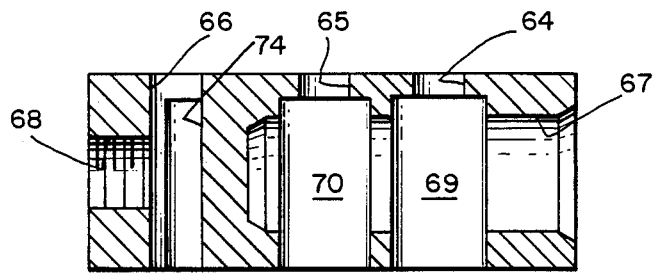
FIG. 6 is a cross-section view of the housing of the gas/saline valve with suction control of FIG. 2 taken along the line 6—6 of FIG. 5.
Figure 5:
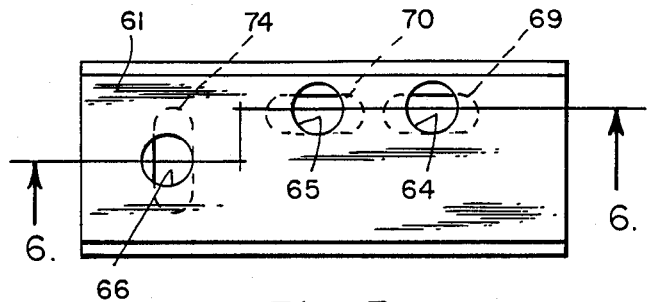
FIG. 5 is a side elevation of the housing of the gas/saline valve with suction control of FIG. 2.

Referring to FIG. 5 in conjunction with FIG. 4 and FIG. 6 the housing 61 includes an open end 67 and a threaded end 68. The housing 61 also includes a first slotted chamber 69 and a second slotted chamber 69. The first and second slotted chambers 69 and 70 are contiguous to the first and second bores 64 and 65, respectively. The first and second tubings 38 and 41 are disposed within the first and second slotted chambers 69 and 70, respectively.

Referring to FIG. 7 in conjunction with FIG. 4, FIG. 8 and FIG. 9 the gas/saline control knob 62 includes a solid cylinder which has a first semi-cylindrical notch 71 and a second semi-cylindrical notch 72. The first and second semi-cylindrical notches 71 and 72, when the solid cylinder is assembled inside the housing 61, are aligned with the first and second slotted chambers 69 and 70, respectively. When the unnotched portion of the solid cylinder is contiguous to the first tubing 38, the unnotched portion compresses the first tubing 38 into the first slotted chamber 69 thereby closing off the flow of gas. When the second semi-cylindrical notch 72 is contiguous to the second tubing 41, the second tubing does not compress the second tubing 41 thereby maintaining the flow of saline therethrough.

Referring to FIG. 10 in conjunction with FIG. 4 when the solid cylinder is rotated 180 the second semi-cylindrical notch 72 becomes contiguous to the first tubing 38 and the unnotched portion of the solid cylinder becomes contiguous to the second tubing 41. The first tubing 38 is no longer compressed thereby turning on the flow of gas therethrough. The unnotched portion compresses the second tubing 41 into the second slotted chamber 70 thereby closing off the flow of saline.

Referring to FIG. 9 in conjunction with FIG. 4 and FIG. 10 the suction control knob 63 includes a solid, threaded cylinder 73. The housing 61 further includes a third slotted chamber 74. The solid, threaded cylinder 73 is threaded into the housing 61 at its threaded end 68. When the solid, threaded cylinder 73 has been threaded to its closed off position, the solid, threaded cylinder 73 compresses the third tubing 47 thereby closing off suction. When the solid, threaded cylinder 73 is unthreaded from its closed off position, the solid, threaded cylinder 73 no longer compresses the third tubing 47 thereby turning on suction.

From the foregoing it can be seen that a gas/saline valve with suction control for use in an insufflation and irrigation system which a surgeon used during diagnostic arthroscopy and arthroscopic surgery in order to distend a knee joint during laser arthroscopic surgery has been described. It should be noted that distances of and between the figures are not to be considered significant.

Accordingly it is intended that the foregoing disclosure and showing made in the drawing shall be considered only as an illustration of the principles of the present invention.

What is claimed is:

1. A gas/saline insufflation system for use with an arthroscopic attachment with a gas inlet and an arthroscope with a saline inlet, said gas/saline insufflation system comprising:
   a. a gas insufflator which provides a flow of gas;
   b. a first tubing in fluid communication with the gas insufflator for being coupled to a gas inlet of the arthroscopic attachment;
   c. a saline source which provides a flow of saline;
   d. a second tubing in fluid communication with said saline source for being coupled to a saline inlet of the arthroscopic attachment;
   e. a housing with an open end which has a first bore and a second bore and which also has a first slotted chamber and a second slotted chamber both of which are contiguous to said first and second bores, respectively, within which said first and second tubings, respectively, are disposed; and
   f. a gas/saline control knob having a solid cylinder which has a first semi-cylindrical notch and a second semi-cylindrical notch and which is rotatively coupled within said housing with said first and second semi-cylindrical notches being aligned with said first and second slotted chambers, respectively, whereby when an unnotched portion of said solid cylinder is contigous to either said first or second tubing, it compresses said tubing into either said first or second slotted chamber thereby closing off either said flow of gas or saline respectively, therein and when either said first or second semi-cylindrical notch becomes contiguous to either said first or second tubing, respectively, said tubing is no longer compressed thereby maintaining or turning on either said flow of gas or saline therethrough.

2. A gas/saline insufflation system with suction control according to claim 1 for use with a suction probe and a suction device wherein said housing has a threaded end, a third bore and a third slotted chamber which is contiguous to said third bore and wherein said gas/saline insufflation system also comprises:
   a. a third tubing in fluid communication with a source of suction, for being coupled to a suction probe; and
   b. a suction control knob with a solid, threaded cylinder which is threaded onto said houding at its said threaded end whereby, when said solid, threaded cylinder has been threaded to its closed off position, said solid, threaded cylinder compresses said third tubing thereby closing off suction and when said solid, threaded cylinder in unthreaded from its closed off position, said solid, threaded cylinder no longer compresses said third tubing thereby either maintaining or turning on suction.

* * * * *